United States Patent [19]
Royce

[11] Patent Number: 5,273,758
[45] Date of Patent: Dec. 28, 1993

[54] DIRECTLY COMPRESSIBLE POLYETHYLENE OXIDE VEHICLE FOR PREPARING THERAPEUTIC DOSAGE FORMS

[75] Inventor: Alan E. Royce, Effort, Pa.
[73] Assignee: Sandoz Ltd., Basel, Switzerland
[21] Appl. No.: 868,073
[22] Filed: Apr. 13, 1992

Related U.S. Application Data
[63] Continuation of Ser. No. 672,503, Mar. 18, 1991, abandoned.
[51] Int. Cl.$^5$ .............................................. A61K 9/20
[52] U.S. Cl. ................................. 424/465; 424/464; 424/486; 424/469
[58] Field of Search ............... 424/464, 465, 469, 486, 424/470

[56] References Cited

U.S. PATENT DOCUMENTS 4,343,789  8/1982  Kawata et al. ................. 424/497
4,996,047  2/1991  Kelleher et al. ................ 424/483

Primary Examiner—Thurman K. Page
Assistant Examiner—James M. Spear
Attorney, Agent, or Firm—Robert S. Honor; Richard E. Vila; Diane E. Furman

[57] ABSTRACT

Polyethylene oxide polymer is employed as a directly compressible binder matrix for therapeutically active dosage forms. Advantageously, the polyethylene oxide has an adjustable rate control effect on the release of medicament from the dosage form, enabling in particular the preparation of sustained release dosage forms.

26 Claims, 1 Drawing Sheet

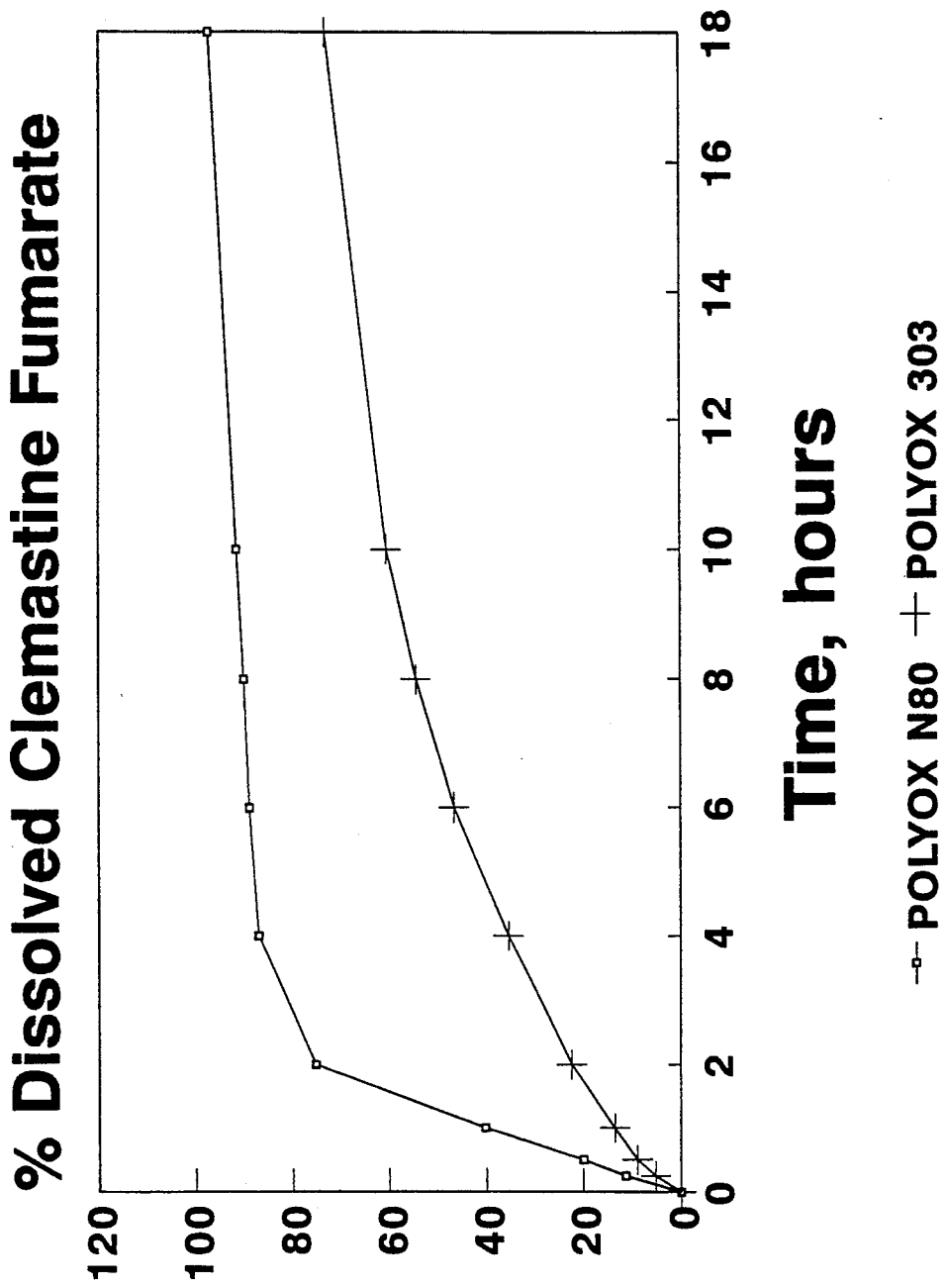

DIRECTLY COMPRESSIBLE POLYETHYLENE OXIDE VEHICLE FOR PREPARING THERAPEUTIC DOSAGE FORMS

This is a continuation of application Ser. No. 07/672,503, field Mar. 18, 1991, now abandoned.

FIELD OF THE INVENTION

This invention relates to compositions to be combined with a therapeutically active medicament and formed into solid, shaped unit dosage forms. More particularly, the present invention relates to compositions comprising a free-flowing directly compressible vehicle which can be blended with a medicament, and to directly compressed dosage forms prepared therefrom.

BACKGROUND OF THE INVENTION

In order to prepare solid, shaped dosage forms from fine particles or powders comprising therapeutic agents, it has generally been necessary to process the powders in a manner to improve their flowability, cohesiveness and other characteristics which will enable the resulting material to be fabricated by conventional processes such as tableting, encapsulation, molding, etc. into a satisfactory unit form that can suitably deliver an agent into the environment of use.

Various processes have therefore been developed for modifying starting powders or other particulate materials, in which typically the powders are gathered together with a binder material into larger permanent free-flowing agglomerates or granules referred to collectively as a "granulation." For example, solvent-assisted "wet" granulation processes are generally characterized in that the powders are combined with a binder material and moistened with water or an organic solvent under conditions to result in formation of a wet granulated mass from which the solvent must then be evaporated. Such processes, while widely employed, have certain recognized limitations arising from the use when necessary of non-aqueous solvents which may be environmentally deleterious, and furthermore may not be readily adaptable in connection with moisture or heat sensitive medicaments. Alternatively, the known "dry granulation" processes, which can depend on fairly complicated milling schemes to produce a suitable granulation, also have acknowledged disadvantages.

A "direct compression" process has in limited cases provided a simpler and more economical means of preparing compressed dosage forms.

In such a process, the therapeutically active ingredient is combined with a binder-diluent or vehicle which itself is characterized in having the requisite properties for tableting, such as flowability, appropriate particle size distribution, binding ability, acceptable bulk and tap density and dissolution properties, and the resulting blend can therefore be "directly" provided to a die cavity or mold for compaction, without prior granulation. See Shangraw, "Compressed Tablets by Direct Compression," in *Pharmaceutical Dosage Forms*, 2d Ed., 1989, Vol. 1, pp. 195-246. The resulting compressed dosage form often provides improved stability and dissociation profiles, as well as batch-to-batch uniformity, relative to "wet" or "dry" granulated dosage forms.

A suitable direct compression vehicle for a given application is preferably also tailored, for example, to be compatible with the active ingredient, to resist physical or chemical change on aging, to be air, moisture and heat-stable, have sufficient capacity for the active ingredient in the dosage form, accept colorants uniformly when necessary, and not interfere with biological availability.

Materials employed by the art which to varying degrees fulfill the requirements of a direct compression vehicle include water soluble materials such as various forms of lactose (e.g., spray-dried lactose, Fast Flow ® lactose, anhydrous lactose), as well as sucrose, dextrose, sorbitol, mannitol and maltodextrin, and relatively insoluble materials such as microcrystalline cellulose (e.g., Avicel ®), starch, dicalcium phosphate dihydrate, and calcium carbonate.

However, such materials, while often comprising a relatively large proportion by weight of the tableted formulation in order to impart full advantage of their compression properties, nevertheless in themselves are generally insufficient to regulate the rate of disintegration of the dosage form or release of the medicament, and therefore must often be accompanied by various additional excipients having such a rate-control effect, the latter which (given practical limitations on the size of the dosage form) may be confined to low concentrations at which the rate control effect is not completely satisfactory.

It has therefore been an object to identify a directly compressible vehicle which can exert a rate control function in the prepared dosage form.

In particular, it has been an object to prepare both immediate and sustained release therapeutically active dosage forms comprising such an excipient.

SUMMARY OF THE INVENTION

It has now been found that directly compressed dosage forms may be prepared from compositions comprising polyethylene oxide as a binder-matrix.

The compositions and dosage forms of the invention comprise about 5 to about 99.99 wt.% of polyethylene oxide polymer, and a therapeutically active medicament dispersed therein.

The therapeutic medicament may comprise from about 0.01 to about 95 wt.% of such compositions.

Advantageously, it has been found that the polyethylene oxide can provide an adjustable rate controlling effect on the release of medicament from the dosage form, and that directly compressed dosage forms may therefore be prepared which can dispense medicament at varying rates.

Further advantageously, the direct compression process of the invention provides a therapeutically active dosage form wherein the medicament is well dispersed, has no loss of activity due to moisture or heat exposure such as may occur during a granulation process, and is substantially free of solvent residues.

BRIEF DESCRIPTION OF THE DRAWING

FIG 1 is a graph depicting the cumulative amount of a medicament dispensed over a prolonged period of time from dosage forms prepared according to the invention.

DETAILED DESCRIPTION OF THE INVENTION

Polyethylene oxide is a nonionic homopolymer of the formula $-(-O-CH_2-CH_2-)-_n$, wherein n represents the average number of oxyethylene groups, n generally being from about 2,000 to about 100,000. It is a water soluble resin which is available as a white powder in several grades which vary in viscosity profile when dissolved in water, National Formulary XVII, pp. 1963–1964 (1990) Molecular weights range from about 100,000 to about 6,000,000, corresponding to a viscosity range of under about 200 cps for a 5% aqueous solution of the lower molecular weight polymers to over about 6,200 cps for a 1% solution of the higher molecular weight polymers. Polyethylene oxide resins are commercially available under the tradename Polyox ® from Union Carbide Corporation. The Polyox ® WSR series corresponds to polymers having a broader distribution of molecular weight ranges than polymers in the WSR N series.

For example, Polyox ® WSR N80 has an average molecular weight of about 200,000, and a 5% aqueous solution thereof at 25° C. has a viscosity on a Brookfield RVT, No. 1 spindle at 50 rpm of about 65 to 115 cps, and a pH of 8 to 10.

Polyox ® WSR 303 has an average molecular weight of about 5,000,000 to 6,000,000, and a 1% aqueous solution thereof at 25° C. has a viscosity of 7,200 to 10,000 cps on a Brookfield RVF, No. 2 spindle at 2 rpm, and a pH of 8 to 10.

Particle size distribution of the above-mentioned Polyox ® resins is such that passage through a 10-mesh sieve is 100%, and through a 20-mesh sieve is about 96%. Other particle size distributions may also be useful in the invention.

See Union Carbide Corp., POLYOX ® WATER-SOLUBLE RESIN Product Specifications (1988).

The use of a particular molecular weight polyethylene oxide polymer as a binder material will depend on the desired disintegration or release rate characteristics to be imparted to the prepared dosage form. In general, lower molecular weight polyethylene oxide polymers, i.e. having MW of up to about 300,000, e.g., Polyox ® N80, may be selected to prepare tablets from which the medicament is released within a relatively short time period, i.e. immediate release tablets. Sustained release dosage forms may be prepared from the higher molecular weight polymers, i.e. having MW higher than about 300,000, especially about 5,000,000 (e.g., Polyox ® 303). It is contemplated that mixtures of varying molecular weight polymers may also be employed as a matrix system to obtain the desired tablet release properties, and such mixtures may comprise respective amounts of the various polyethylene oxide polymers as shall be within the skill of the worker in the art to ascertain to provide the appropriate release pattern.

Other optional components of the compositions of the invention include various binders, disintegrants, diluents, etc., including cellulose ethers, such as hydroxypropyl methylcellulose, and waxy substances, as well as minor amounts of various lubricants such as talc, colloidal silicon dioxide, stearic acid or metal stearates, etc., and colorants, sweeteners, and the like.

The compositions of the invention comprise from about 5 to 99.99 wt.%, and preferably 20 to 99.99 wt.%, of free-flowing, directly compressible polyethylene oxide binder material.

In one embodiment, the compositions consist essentially of the polyethylene oxide binder and the medicament.

The dosage forms are prepared by a direct compression process; that is, the process comprises, and in one embodiment, consists essentially of, the steps of (i) dry blending particles comprising 5 to 99.99 wt.%, and preferably 20 to 99.99 wt.%, of polyethylene oxide with the therapeutic medicament, as well as other optional excipients, and (ii) providing the resulting mixture to a compression machine, and applying sufficient pressure to the composition to form a unitary dosage form.

The medicament may be employed in powder, crystalline, or other form, and typically need not be compounded to an amorphous or other type granulated form.

The polyethylene oxide and medicament and other optional ingredients are dry blended, i.e. in the absence of added solvents or heat, to produce a free-flowing material wherein the medicament is well dispersed in the polyethylene binder-matrix.

The mixture is then provided to, for example, a tableting machine and a compression force of about 0.5 to 10 tons is applied.

A tableted dosage form is therefore prepared, in which the medicament is generally evenly dispersed throughout the polyethylene oxide binder, and which is free of solvent residues.

As used herein, the term "tablet" refers to a compressed body which is composed of a plurality of discrete particles, and includes pills, lozenges, dragee cores, capsule slugs, molded forms, and the like.

The tableted dosage forms of the invention can provide relatively immediate or more sustained release of the therapeutic medicament into the environment.

The expression "therapeutic medicament" or "drug" shall include any physiologically or pharmacologically active substance that produces a local or systemic effect(s) in animals, which include warm-blooded mammals, humans, primates, etc.

The term "physiological" as used herein denotes the administration of a drug to effect normal levels and functions. The term "pharmacological" denotes variations in response to the amount of drug administered to the host. The devices have found a particular use as vehicles for various human and animal drugs, particularly for the oral administration thereof, although for other systems as well, including systems such as buccal, implant, nose, artificial gland, rectum, cervical, intrauterine, occular, arterial, venous, ear and the like, may be manufactured according to the process of the invention.

The active drugs that can be delivered include inorganic and organic drugs, without limitation, drugs that act on the central nervous system, cardiovascular drugs, endocrine drugs, drugs for metabolic disorders, immunologic drugs, and drugs for treatment of allergies and infectious diseases. More particularly, such drugs may comprise depressants, hypnotics, sedatives, psychic energizers, tranquilizers, anti-hypertensives, anticonvulsants, muscle relaxants, antiparkinson agents, analgesics, anti-inflammatory, local anesthetics, muscle contractants, anti-microbials, anti-malarials, hormonal agents, contraceptives, sympathomimetics, diuretics, anti-parasitics, neoplastics, hypoglycemics, ophthalmics, electrolytes, diagnostic agents, and the like.

Compositions according to the invention may be prepared which comprise clemastine fumarate in free base form, or in a pharmaceutically acceptable acid addition salt form. Clemastine fumarate, i.e., (1) Pyrrolidone, 2-[2-[1-(4-chlorophenyl)-1-phenylethoxy]ethyl]-1-methyl-, [R-(R*,R*)]-, (E)-2-butenedioate; (2) (+)-(2R)-2-[2-[[(R)-p-Chloro-α-methyl-α-phenylbenzyl]-oxy]-ethyl]-1-methylpyrrolidone fumarate, is a colorless to faintly yellow, practically odorless, crystalline powder. It belongs to the benzhydryl ether group of antihistaminic compounds and has activity as an $H_1$- receptor antagonist (CAS 14976-57-9; CAS-15686-51-8).

The following examples are merely intended to be illustrative of the invention and not limitative thereof. Unless otherwise expressly indicated the chemical substances used are in the National Formulary or the U.S. Pharmacopeia.

EXAMPLE 1

2.68 mg. clemastine fumarate, available from Sandoz Corp. under the tradename Tavist ®, is combined with 177.32 mg. of polyethylene oxide having a molecular weight of (a) 200,000 (Polyox ® N80, Union Carbide) or (b) 6,000,000 (Polyox ® 303, Union Carbide), and passed through a 60-mesh screen. The blended powders are then compressed into tablets on a hand-operated Carver press. A compaction force of 1 ton is applied.

Two tablets, prepared as in (a) and (b) above, are subjected to dissolution studies according to the method described in *U.S. Pharmacopoeia* (1985) Vol. XXI, pp. 1243-1244.

A multiple position dissolution stirrer such as that described at USP p. 1244, Apparatus 2, is employed, which is equipped with a Teflon paddle (20 rpm) in each of six vessels. A dissolution medium comprising 900 ml. of deaerated and distilled water is maintained at 37°±0.5° C. A tablet is sequentially dropped into each vessel. Stirring and timing (time zero) is commenced as the first tablet hits the bottom of the vessel (under the paddle).

At regular intervals, aliquots of test solution are withdrawn from each of the vessels in the order in which the tablets were originally dropped, using a stainless steel cannula. The aliquots are withdrawn from a point midway between the surface of the dissolution medium and the top of the paddle and not less than 1 cm. from each vessel wall.

The amount of clemastine fumarate present in each of the vessels is calculated by reference to standard solutions using UV spectroscopy.

Accompanying FIG. 1 depicts the cumulative amount of medicament delivered by each tablet over an extended period of time.

It will be seen that the tablets of the invention provide a gradual, controlled release of the medicament over an extended period of time.

EXAMPLE 2

Placebo tablets, each 4.9 mg., are prepared in a batch by mixing 98.7 mg of polyethylene oxide having a molecular weight of (a) about 200,000 (Polyox ® N80) or (b) about 6,000,000 (Polyox ® 303), with 11.0 mg. of hydroxypropyl methylcellulose (Pharmocoat 606) and 0.27 mg of magnesium stearate, in a free-fall blender, and then compressing the blend on a high speed tablet press (Manesty, Betapress).

For the tablets prepared according to (a) above, i.e. comprising polyethylene oxide having a molecular weight of about 200,000, a compressive strength (hardness) and weight variation are obtained which indicate that the flowability of the formulation is adequate for the direct tableting process. The disintegration times for the tablets using the USP method of Example 1 range from 30-45 min., indicating that relatively immediate release of a medicament can be effected by the tablets.

For the tablets prepared according to (b) above, i.e. comprising polyethylene oxide having a molecular weight of about 6,000,000 (Polyox ® 303), the compression results are equivalent to those of the tablets prepared in (a). However, these higher molecular weight polyethylene oxide-based tablets do not disintegrate under standard testing procedures, indicating suitability as a sustained release dosage form.

What is claimed is:

1. A direct compression process for preparing a tableted pharmaceutical dosage form consisting of the steps of:
   a. blending a powder for crystalling therapeutic medicament with a direct compression vehicle consisting essentially of polyethylene oxide, in the absence of added solvent or heat, to form a composition in which the medicament in dispersed; and
   b. compresseing the resulting composition under sufficient pressure to form a tablet.

2. A process according to claim 1 wherein the composition comprises 0.01 to 95 wt.% medicament.

3. A process according to claim 2 wherein the composition comprises 5 to 99.99 wt.% polyethylene oxide.

4. A process according to claim 1 wherein the polyethylene oxide is selected from polymers having an average molecular weight of up to about 300,000, polymers having an average molecular weight of about 300,000 or greater, and mixtures thereof.

5. A process according to claim 1 wherein the medicament comprises from about 0.01 to about 95 wt.% of the dosage form.

6. A direct compression process for preparing a tableted pharmaceutical dosage form consisting essentially of the steps of:
   a. blending the medicament clemastine fumarate in free base or pharmaceutically acceptable acid addition salt form with a direct compression vehicle comprising polyethylene oxide, in the absence of added solvent or heat, to form a composition in which the medicament is dispersed; and
   b. compressing the resulting composition under sufficient pressure to form a tablet.

7. A process according to claim 6 wherein the polyethylene oxide has the formula $-(O-CH_2-CH_2)_n-$ wherein n represents the average number of oxyethylene groups, and n is 2,000 to 100,000.

8. A process according to claim 6 wherein the polyethylene oxide has an average molecular weight of 100,000 to 6,000,000.

9. A process according to claim 8 wherein the polyethylene oxide has a viscosity of under about 200 cps for a 5% aqueous solution thereof.

10. A process according to claim 8 wherein the polyethylene oxide has a viscosity over about 6,200 cps for a 1% aqueous solution thereof.

11. A process according to claim 8 wherein the polyethylene oxide has a viscosity of 65 to 115 cps for a 5% aqueous solution thereof at 25° C. on a Brookfield RVT, No. 1 spindle at 50 rpm.

12. A process according to claim 8 wherein the polyethylene oxide has a viscosity of 7,200 to 10,000 cps for a 1% aqueous solution thereof at 25° C. on a Brookfield RVF, No. 2 spindle at 2 rpm.

13. A process according to claim 6 wherein the composition comprises 0.01 to 95 wt.% medicament.

14. A process according to claim 6 wherein the composition comprises 5 to 99.99 wt.% polyethylene oxide.

15. A process according to claim 1 wherein the polyethylene oxide has the formula $-(O-CH_2-CH_2)_n-$ wherein n represents the average number of oxyethylene groups, and n is 2,000 to 100,000.

16. A process according to claim 1 wherein the polyethylene oxide has an average molecular weight of 100,000 to 6,000,000.

17. A process according to claim 16 wherein the polyethylene oxide has a viscosity of under about 200 cps for a 5% aqueous solution thereof.

18. A process according to claim 16 wherein the polyethylene oxide has a viscosity over about 6,200 cps for a 1% aqueous solution thereof.

19. A process according to claim 16 wherein the polyethylene oxide has a viscosity of 65 to 115 cps for a 5% aqueous solution thereof at 25° C. on a Brookfield RVT, No. 1 spindle at 50 rpm.

20. A composition according to claim 16 wherein the polyethylene oxide has a viscosity of 7,200 to 10,000 cps for a 1% aqueous solution thereof at 25° C. on a Brookfield RVF, No. 1 spindle at 2 rpm.

21. A process according to claim 1 wherein the polyethylene oxide has an average molecular weight of about 200,000.

22. A process according to claim 1 wherein the polyethylene oxide has an average molecular weight of about 5,000,000 to 6,000,000.

23. A process according to claim 1 wherein the particles comprise about 20 to 99.99 wt.% polyethylene oxide.

24. A process according to claim 16 wherein the composition comprises 0.01 to 95 wt.% medicament.

25. A process according to claim 24 wherein the composition comprises 5 to 99.99 wt.% polyethylene oxide.

26. A process according to claim 1 wherein the medicament comprises clemastine fumarate in free base or pharmaceutically acceptable acid addition salt form.

* * * * *

UNITED STATES PATENT AND TRADEMARK OFFICE
CERTIFICATE OF CORRECTION

PATENT NO. : 5,273,758
DATED : December 28, 1993
INVENTOR(S) : Alan E. Royce

It is certified that error appears in the above-identified patent and that said Letters Patent is hereby corrected as shown below:

Col. 6, l. 10: delete "for" and insert therefor -- or --.

Col. 6, l. 10: delete "crystalling" and insert therefor -- crystalline --.

Col. 6, l. 14: delete "in" and insert therefor -- is --.

Col. 6, l. 15: delete "compresseing" and insert therefor -- compressing --.

Signed and Sealed this

Twentieth Day of September, 1994

Attest:

BRUCE LEHMAN

Attesting Officer

Commissioner of Patents and Trademarks